United States Patent
Cermak et al.

(10) Patent No.: US 8,257,401 B2
(45) Date of Patent: Sep. 4, 2012

(54) BOTTOM MOUNTED PEDICAL SCREW ASSEMBLY

(75) Inventors: Adam Cermak, Alexandria, VA (US);
Jeffrey Johnson, Flowood, MS (US);
Gil Aust, Huntsville, MS (US)

(73) Assignee: Spinal U.S.A., Pearl, MS (US)

( * ) Notice: Subject to any disclaimer, the term of this patent is extended or adjusted under 35 U.S.C. 154(b) by 524 days.

(21) Appl. No.: 12/369,909

(22) Filed: Feb. 12, 2009

(65) Prior Publication Data
US 2009/0210015 A1     Aug. 20, 2009

Related U.S. Application Data

(60) Provisional application No. 61/027,876, filed on Feb. 12, 2008.

(51) Int. Cl.
*A61B 17/70* (2006.01)

(52) U.S. Cl. ........................................ 606/267; 606/270

(58) Field of Classification Search .................. None
See application file for complete search history.

(56) References Cited

U.S. PATENT DOCUMENTS
2005/0273099 A1 * 12/2005 Baccelli et al. ................. 606/61
* cited by examiner

*Primary Examiner* — Brian Pellegrino
*Assistant Examiner* — Rebecca Straszheim
(74) *Attorney, Agent, or Firm* — Cermak Nakajima LLP; Adam J. Cermak

(57) ABSTRACT

A bone screw, which can be a pedicle screw, is generally tulip-shaped. A bore in the bottom of the tulip permits a threaded shaft to be partially inserted into the open interior of the tulip. A seat is formed on the threaded shaft and receives the bottom of the tulip, and prevents the threaded shaft from being inserted too far into the tulip. A saddle is positioned in the interior of the tulip and receives the end of the threaded shaft on one end and can include a trough on its opposite face which can receive a rod that connects together two or more such assemblies. A retaining screw threads into the upper interior surface of the tulip to hold the subcomponents together.

11 Claims, 1 Drawing Sheet

BOTTOM MOUNTED PEDICAL SCREW ASSEMBLY

This application claims priority under 35 U.S.C. §119 to U.S. provisional application No. 61/027,876, filed 12 Feb. 2008, the entirety of which is incorporated by reference herein.

BACKGROUND

1. Field of Endeavor

The present invention relates to medical devices and processes used in bone fixation, and more specifically to bone screws.

2. Brief Description of the Related Art

Bone screws, including pedicle screws, have been used for years to provide an anchor into bone in order to secure other devices to the bone. While advances have been made in such bone screws, current designs do not accommodate all uses and anatomy. For example, U.S. Pat. No. 5,207,678, issued to Harms et al., describes a bone screw assembly that requires the bone screw itself to be assembled with other parts of the device prior to driving the bone screw into bone. While this configuration has been quite popular, in some circumstances it can be desirable to position the bone screw itself in the desired location in bone, and thereafter assemble the remaining elements of the bone screw assembly. Because the bone screw assembly described in the '678 patent includes a top-mounted screw, that is, one in which the bone screw 2 must be inserted through the top of its housing 6 before driving the screw 2 into bone, the practitioner must drive the bone screw with the housing 6 loosely attached to the proximal end of the screw, thus potentially interfering with driving the screw and obstructing the practitioner's view of the screw head and the bone insertion point.

There remains a need for bone screws which can be used to anchor other devices to bone which address, and even overcome, some or all of the deficiencies in the prior art devices.

SUMMARY

According to a first aspect of the invention, a polyaxial bone screw assembly comprises a generally cup-shaped tulip having a top opening, a bottom bore, a semi-spherical inner bottom surface, and a semi-spherical outer bottom surface, a saddle sized to be received in the tulip, the saddle having a semi-spherical outer bottom surface and a recess extending upwardly from said bottom surface, a bone screw having a distal end and a proximal end, a threaded shaft extending proximally from the distal end, a laterally extending platform positioned distal of the proximal end, and a post extending proximally of the platform, the platform including a semi-spherical proximal surface, wherein the bone screw post and the saddle include a snap fit, the snap fit including a recess in one of the bone screw post and the saddle and an enlargement on the other of the bone screw post and the saddle, the enlargement received in the recess.

According to another aspect of the present invention, a method of installing a bone screw assembly in a bone comprises providing a bone screw assembly including a threaded bone screw having a laterally extending platform, a cup-shaped tulip having a proximal opening and a distal opening, and a saddle having a distal bore, moving the bone screw into the bone, positioning the tulip over a proximal portion of the bone screw and proximally of the platform, positioning the saddle inside the tulip, and securing the saddle to said proximal portion of the bone screw.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which.

DETAILED DESCRIPTION OF EXEMPLARY EMBODIMENTS

Figure 1:
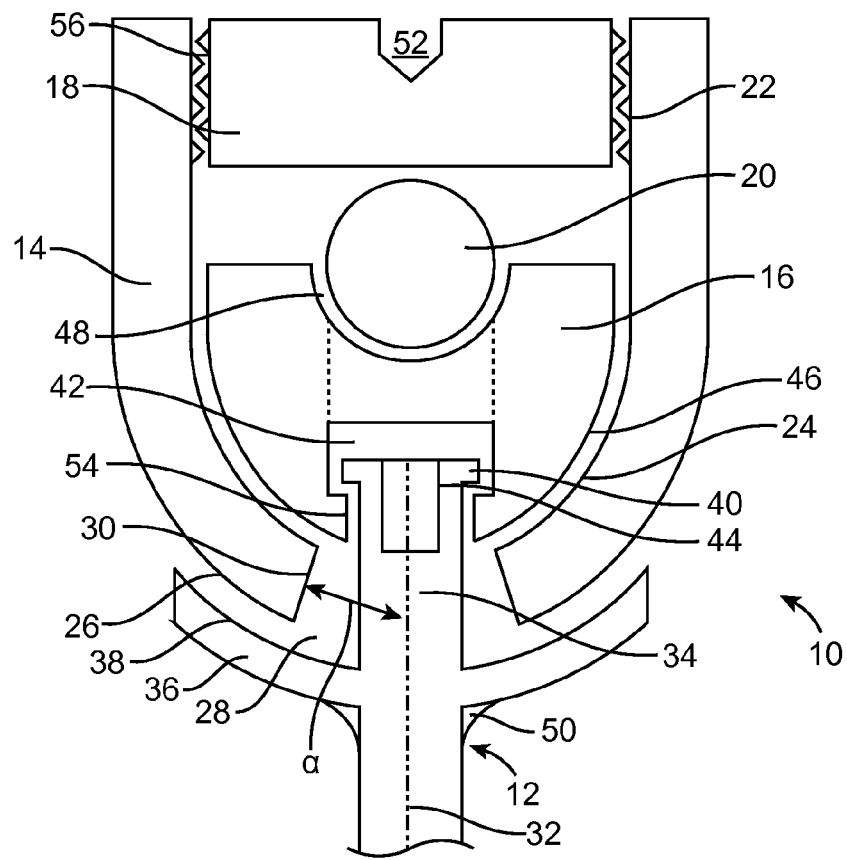
FIG. 1 illustrates a longitudinal cross-sectional view of proximal portions of an exemplary bone screw assembly.

Referring to the drawing figures, like reference numerals designate identical or corresponding elements throughout the several figures. The exemplary embodiment illustrated in FIG. 1 will first be discussed. In the drawing figures, the term "proximal" will refer to the portions of the devices towards the top of the drawings, and the term "distal" will refer to the portions of the devices towards the bottom of the drawings. Unless otherwise stated, the devices are rotationally symmetrical about a longitudinal axis that extends between the proximal and distal ends of the devices.

10 designates the entire bottom mounted pedicle screw assembly of the first embodiment.

12 designates the bone screw portion per se of the assembly 10, which extends distally of the assembly.

14 designates the proximal 'tulip' portion of the assembly 10. The tulip is generally tulip-shaped with two laterally opposed slots in the sidewalls, in the same manner as currently commercially available pedicle screw assemblies; those slots are out of the plane of the sectional view of FIG. 1 and can therefore not be seen in the figure. The slots advantageously are open-ended and extend distally from the proximal end of the tulip 14 toward a distal closed end. The rod 20, described below, extends laterally through those slots.

16 designates the saddle portion of the assembly 10, which also functions to transfer load between the rod (from the retaining and load screw 18, described below) to the lower portions of the tulip 14. The saddle 16 is preferably rotationally symmetrical about the longitudinal axis of the assembly 10, except for the provision of an optional laterally extending trough 48 configured to receive the rod 20.

18 designates the retaining and load screw, which is externally threaded and mates with corresponding threads on the interior, upper surface of the tulip 22, in a manner similar to currently commercially available pedicle screw assemblies. Alternatively, the screw 18 can be an internally threaded nut, and the tulip 14 can alternatively include mating threads on its upper exterior surface.

20 designates a transversely extending rod that is clamped between the screw 18 and the saddle 16, and which extends between and therefore joins together two or more assemblies 10 in a manner well known to the routineer in the art.

22 designates the thread on the interior surface of the tulip 14.

24 designates a semi-spherical concave interior seat surface of the tulip 14, against which the correspondingly shaped, convex exterior surface of the adjacent saddle 16 bears when the saddle 16 is pressed against the bottom interior surface of the tulip.

26 designates a semi-spherical convex exterior bearing surface of the tulip 14, against which the correspondingly shaped, concave interior surface of the adjacent platform 36 of the bone screw 12 bears.

28 designates a bore through the bottom of the tulip 14, through which the post 34 of the bone screw 12 extends. The radial or lateral size of the bore 28 is at least large enough for the post 34 to be inserted through the bore from the bottom of the tulip 14. The radial size of the bore 28 is selected to permit the assembly 10 to be polyaxial, that is, to permit the tulip to pivot about the longitudinal axis of the bone screw 12 while still being clamped between the saddle 16 and the platform 36.

30 designates the inner surface of the tulip 14 which defines the bore 28.

32 designates the threaded shaft of the bone screw 12, the threads per se not being illustrated so as to not obscure aspects of the invention. Also not illustrated is the pointed distal end of the bone screw 12.

34 designates the proximal post of the bone screw 12, which extends proximally from the platform 36. The post 34 has a longitudinal length sufficient to extend through the bore 28 and into a recess 42 in the saddle 16 when the bone screw 12 is positioned partially inside the tulip and the platform 36 bearing against the distal face 26 of the tulip.

36 designates the platform of the bone screw 12 against which the lower portions of the tulip 14 bear and are clamped. The platform is illustrated as being generally cup-shaped; however, the distal surfaces can be rounded, as illustrated, squared, or any other shape. The lateral size of the platform, that is, the distance between the outer lateral tip of the platform to the shaft 32, is selected in conjunction with the size of the bore 28, the lateral cross-sectional radius of the post 34, and other dimensions of the assembly, to maximize the amount of the tulip 14 that is clamped between the saddle 16 and the platform, for a predetermined maximum pivot angle for the tulip to function as a polyaxial assembly. In the illustration of FIG. 1, which is otherwise generally not to scale, an angle a of between 10 and 15 degrees of pivot is illustrated. Optionally, the platform can be formed of at least three laterally extending arms, rather than a circumferentially continuous structure.

38 designates a semi-spherical, upper, concave surface of the platform 36, against which the correspondingly shaped, convex lower exterior surface of the adjacent tulip 14 bears.

40 designates an enlargement at the proximal end of the post 34. The enlargement 40 cooperates with lower portions of the saddle 16 to snap and retain the saddle onto the post, while also optionally permitting the saddle to freely rotate about the longitudinal axis of the post, after the post has been inserted through the bore 28. While illustrated to include a rectangular, laterally extending lip, the enlargement 40 can take any shape that permits it to snap fit with the saddle, and to be inserted through the bore 28 from the bottom of the tulip 14.

42 designates a recess in the center of the saddle 16, into which the enlargement 40 is snapped to retain the saddle to the post 34 and, therefore, the tulip 14 sandwiched between the platform 36 and the saddle. The longitudinal depth of the recess 42 is selected so that the enlargement 40 does not interfere with the saddle 16 moving downward (distally) relative to the tulip 14, to clamp the tulip between the saddle and the platform. Preferably, the recess 42 extends longitudinally completely through the saddle, as indicated by the broken line through the center of the saddle 16, making it a through bore with upper (proximal) and lower (distal) openings, to permit a user to insert a torque driver (e.g., a screwdriver) through the saddle and into engagement with portions of the post 34, so that the bone screw 12 can be driven into bone by the practitioner, if the assembly 10 is preassembled with the bone screw 12, tulip 14, and saddle 16 already snapped together. Alternatively, the recess 42 can be a blind bore.

44 designates a blind bore in the upper (proximal) portion of the post 34, which includes a non-circular inner surface configured so that a torque driver can be inserted into the bore 44 to rotate and longitudinally drive the bone screw into bone.

46 designates a semi-spherical convex lower exterior bearing surface of the saddle 16, against which the correspondingly shaped, concave interior surface of the adjacent tulip 14 bears.

48 designates an optional trough in the upper surface of the saddle 16, in which the rod 20 is positioned and is clamped by the saddle and the screw 18. While the exact shape of the trough is not critical, a concave shape as illustrated is preferred; a V-notch could also easily and expeditiously be used. The trough is sized to receive the rod 20.

50 designates one or more optional reinforcements between the platform 36 and the bone screw 12.

52 designates a blind bore in the upper (proximal) surface of the screw 18, configured to receive a torque driver in much the same manner as bore 44.

54 designates a radially inwardly extending lip on the inner surface of the recess 42. The lip 54 is configured to act with the enlargement 40 on the post 34 to form a snap fit between the saddle and the post. The lip 54 can optionally be circumferentially continuous, or can be circumferentially discontinuous in the form of at least three fingers that extend radially inwardly from the saddle 16.

56 designates the threads on the outer surface of the screw 18.

Figure 2:
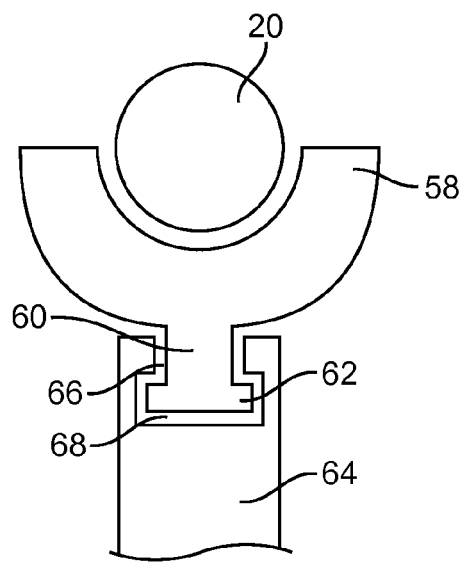
FIG. 2 illustrates a longitudinal cross-sectional view of proximal portions of a second exemplary bone screw assembly.

In the exemplary embodiment illustrated in FIG. 2, in which the tulip 16 and platform 36 are not illustrated:

58 designates a saddle similar in most respects to the saddle 16, except that it includes a downwardly (distally) extending post 60 having an enlargement 62.

60 designates the post of the saddle 58.

62 designates the enlargement of the post 60.

64 designates the post of the bone screw 12.

66 designates a blind bore in the proximal end of the post 64, sized to receive the post 60 therein to form a snap fit, while being deep enough so that the saddle 58 can move downward (distally) as described above.

68 designates an enlarged portion of the bore 66, sized to receive the post 60 and the enlargement 62 to form a snap fit. As with the embodiment illustrated in FIG. 1, the structures which form the snap fit can take a number of forms. As with the embodiment of FIG. 1, the embodiment of FIG. 2 includes bores similar to bores 42, 44, to permit a torque driver to be inserted through the saddle 58, post 60, and into the post 64, to permit the practitioner to drive the bone screw into bone.

With reference to FIG. 1, exemplary methods of using a bone screw assembly will now be described. The practitioner identifies a location in bone, e.g., a pedicle of a patient's spine, in which it is desired to install a bone screw. The bone screw 12 is positioned at that location, with a torque driver (not illustrated) engaged in the bore 44, and the bone screw is driven into the bone. After the bone screw 12 is in place, at least partially, in the bone, the tulip 14 is positioned on the screw, with the post 34 extending through the bore 28. The saddle 16 is then positioned inside the tulip. In order to secure the saddle 16 to the post 34, a distally directed force must be applied to the saddle, so that the lip 54 can ride over the enlargement 40; this force can be supplied by the screw 18, or can be applied by the practitioner directly to the proximal surfaces of the saddle.

Once the saddle 16 and screw 12 have been secured together, the tulip 14 will have been captured between them, and more specifically between the platform 36 and the saddle. Because of the cooperating semi-spherical surfaces of the saddle, tulip, and platform, the tulip 14 can pivot about the longitudinal axis of the screw 12 while still retained on the screw, thus permitting the assembly 10 to be polyaxial.

With the saddle 16 attached to the post 34, the cylindrical bar 20, known to the routineer in the art and useful to connect together at least two, e.g., pedicle screw assemblies, is positioned over the proximal surface of the saddle, advantageously in the optional trough 48, and the retaining screw 18 is put in place. Distal motion of the retaining screw 18 causes the retaining screw to bear distally on the proximal portion of the bar 20, causing the bar 20 to be forced distally against the saddle 16, which in turn is free to move distally over the post 34 because of the longitudinal size of the bore 42 and bear against the surface 24 of the tulip 14, which is turn causes the tulip to bear down distally against the surface 38 of the platform 36. Because the platform 36 is secured to bone, the force generated by the retaining screw 18 causes the tulip 14 to be clamped between the saddle and the screw 12, while still permitting the tulip to assume angled orientations relative to the screw 12.

Optionally, the saddle 16, tulip 14, and screw 12 can be pre-assembled, that is, the saddle and post 34 secured together with the tulip trapped between them, before the practitioner drives the screw 12 into bone. In this alternative, the practitioner's torque driver is positioned in a throughbore 42 in the saddle to drive the screw 12.

With reference to FIG. 2, the same general process is used to mount the assembly to bone as that used with the embodiment of FIG. 1, with the practitioner's torque driver used to drive the bone screw 12 at post 64, optionally through the saddle and the post 60.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A polyaxial bone screw assembly comprising:
   a generally cup-shaped tulip having a top opening, a bottom bore, a semi-spherical inner bottom surface, and a semi-spherical outer bottom surface;
   a saddle sized to be received in the tulip, the saddle having a semi-spherical outer bottom surface;
   a bone screw having a distal end and a proximal end, a threaded shaft extending proximally from the distal end, a laterally extending platform positioned distal of the proximal end, and a post extending proximally of the platform, the platform including a semi-spherical proximal surface;
   wherein the bone screw post and the saddle are both configured and arranged to form a snap fit connection, the snap fit connection including a recess in one of the bone screw post and the saddle and an enlargement on the other of the bone screw post and the saddle, the enlargement received in the recess.

2. The bone screw assembly according to claim 1, further comprising a retaining screw having a thread, and wherein the tulip further comprises a thread configured and arranged to mate with the retaining element thread.

3. The bone screw assembly according to claim 2, the retaining screw thread comprises an external thread, the tulip comprises a proximal inner surface, and the thread of the tulip is on the tulip proximal inner surface.

4. The bone screw assembly according to claim 3, further comprising a bar extending laterally through the tulip between the retaining screw and the saddle.

5. The bone screw assembly according to claim 1, wherein the saddle comprises said recess, and said recess comprises a blind bore.

6. The bone screw assembly according to claim 1, wherein the saddle comprises said recess, and said recess comprises a throughbore.

7. The bone screw assembly according to claim 1, wherein the recess is in the saddle and the enlargement is on the bone screw post.

8. The bone screw assembly according to claim 1, wherein the recess is in the bone screw post and the enlargement is on the saddle.

9. The bone screw assembly according to claim 1, wherein the bone screw platform is laterally larger than the tulip bottom bore.

10. The bone screw assembly according to claim 1, wherein the tulip bottom bore and the bone screw post are mutually sized so that the tulip can pivot relative to the bone screw.

11. The bone screw assembly according to claim 1, wherein the tulip bottom bore and the bone screw post are mutually sized so that the tulip can pivot relative to the bone screw up to about 15 degrees.

\* \* \* \* \*